US008749775B2

(12) United States Patent
Verstappen et al.

(10) Patent No.: US 8,749,775 B2
(45) Date of Patent: Jun. 10, 2014

(54) INSPECTION METHOD AND APPARATUS

(75) Inventors: Leonardus Henricus Marie Verstappen, Weert (NL); Arie Jeffrey Den Boef, Waalre (NL)

(73) Assignee: ASML Netherlands B.V., Veldhoven (NL)

(*) Notice: Subject to any disclaimer, the term of this patent is extended or adjusted under 35 U.S.C. 154(b) by 332 days.

(21) Appl. No.: 12/882,631

(22) Filed: Sep. 15, 2010

(65) Prior Publication Data

US 2011/0085162 A1 Apr. 14, 2011

Related U.S. Application Data

(60) Provisional application No. 61/251,031, filed on Oct. 13, 2009.

(51) Int. Cl.
*G01N 21/00* (2006.01)

(52) U.S. Cl.
USPC ............................................... 356/237.5

(58) Field of Classification Search
USPC ............................................ 356/237.2, 237.5
See application file for complete search history.

(56) References Cited

U.S. PATENT DOCUMENTS

| 5,751,243 | A | * | 5/1998 | Turpin ..................... 342/179 |
| 6,137,570 | A | | 10/2000 | Chuang et al. |
| 6,191,849 | B1 | * | 2/2001 | Maeshima et al. ......... 356/237.1 |
| 6,510,395 | B2 | | 1/2003 | Stanke |
| 6,791,099 | B2 | | 9/2004 | Some et al. |
| 6,986,280 | B2 | | 1/2006 | Muckenhirm |
| 7,528,944 | B2 | * | 5/2009 | Chen et al. ............... 356/237.6 |
| 7,567,344 | B2 | * | 7/2009 | LeBlanc et al. ........... 356/239.1 |
| 8,189,195 | B2 | | 5/2012 | Den Boef et al. |
| 2003/0227618 | A1 | * | 12/2003 | Some ..................... 356/237.1 |
| 2007/0201017 | A1 | | 8/2007 | Opsal et al. |
| 2008/0117434 | A1 | | 5/2008 | Verstappen et al. |
| 2008/0218767 | A1 | | 9/2008 | Mos et al. |
| 2008/0279442 | A1 | | 11/2008 | Den Boef et al. |
| 2009/0213215 | A1 | * | 8/2009 | Shibata et al. ............. 348/92 |

FOREIGN PATENT DOCUMENTS

| CN | 1155078 A | 7/1997 |
| CN | 1214116 A | 4/1999 |
| CN | 1496478 A | 5/2004 |
| CN | 1908638 A | 2/2007 |

(Continued)

OTHER PUBLICATIONS

Allgair, J. et al., "Manufacturing Considerations for Implementation of Scatterometry for Process Monitoring," *Metrology, Inspection, and Process Control for Microlithography XIV.* 3998:125-134, Proceedings of the SPIE —The International Society for Optical Engineering, USA (2000).

International Search Report and Written Opinion directed to related International Patent Application No. PCT/EP2010/063184, mailed on Nov. 29, 2010 from the International Searching Authority, European Patent Office, Rijswijk, Netherlands; 14 pages.

(Continued)

*Primary Examiner* — Roy M Punnoose
(74) *Attorney, Agent, or Firm* — Sterne, Kessler, Goldstein & Fox P.L.L.C (57) ABSTRACT

A method and apparatus is used for inspection of devices to detect processing faults on semiconductor wafers. The method includes illuminating a strip of a die along a scan path with a moving measurement spot. The method further includes detecting scattered radiation to obtain an angle-resolved spectrum, and comparing the scattering data with a library of reference spectra. Based on the comparison, the method includes determining the presence of a fault of the die at the strip. The illumination and detection are performed along the scan path across a region, such that the scattering data is spatially integrated over the region.

19 Claims, 6 Drawing Sheets

(56) References Cited

FOREIGN PATENT DOCUMENTS

| | | |
|---|---|---|
| CN | 101473218 A | 7/2009 |
| EP | 1 329 686 A2 | 7/2003 |
| EP | 1 628 164 A2 | 2/2006 |
| EP | 1 628 184 A1 | 2/2006 |
| JP | 05-281148 A | 10/1993 |
| JP | 2003-294436 A | 10/2003 |
| JP | 2009-038339 A | 2/2009 |
| NL | 1036734 A1 | 10/2009 |
| WO | WO 02/080264 A2 | 10/2002 |

OTHER PUBLICATIONS

English-Language Abstract for Chinese Patent Publication No. 1155078 A, published Jul. 23, 1997; 1 page.

English-Language Abstract for Chinese Patent Publication No. 1214116 A, published Apr. 14, 1999; 1 page.

English-Language Abstract for Chinese Patent Publication No. 1908638 A, published Feb. 7, 2007; 1 page.

English-Language Abstract for Japanese Patent Publication No. 05-281148 A, published Oct. 29, 1993; 1 page.

* cited by examiner

INSPECTION METHOD AND APPARATUS

CROSS REFERENCE TO RELATED APPLICATIONS

This application claims priority under 35 U.S.C. §119(e) to U.S. Provisional Patent Application No. 61/251,031, filed Oct. 13, 2009, which is incorporated by reference herein in its entirety.

BACKGROUND

1. Field of the Invention

The present invention relates to methods of inspection and apparatus usable, for example, in the manufacture of devices by lithographic techniques. The invention may be applied for example to detect processing faults on semiconductor wafers arising during processing by a lithographic apparatus.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Two known approaches for inspecting a semiconductor wafer after processing by a lithographic apparatus are: 1. Fast inspection for defects with dense sampling to look for anomalies on the wafer; and 2. Critical Dimension (CD) and Overlay (OV) metrology on a few selected sites where a detailed (and therefore time consuming) measurement is done of the resist profile and the overlay.

For Integrated Metrology (IM) of CD it would be preferable to measure all wafers in a lot and cover as much wafer area as possible since this gives the highest chance of detecting localized process excursions, however the time spent performing such measurements needs to be considered. Move Acquire Measure (MAM) time is a figure of merit for methods of inspecting semiconductor wafers. The MAM time includes: time spent moving the wafer between measurement sites; time spent aligning the measurement target to the inspection apparatus at the measurement site; and time spent acquiring the measurement. MAM time for CD is of the order of 300-3000 ms at best (depending on the application) which is too long to measure all wafers in a lot with sufficient wafer coverage. This increases the chance of missing the relevant locations on the wafer where large process excursions may be present.

SUMMARY

An embodiment of the present invention provides a method comprising the following steps. Illuminating a region of a substrate with a radiation beam. Detecting scattered radiation to obtain first scattering data. Comparing the first scattering data with second scattering data. Determining, based on the comparison, the presence of a fault of the substrate at the region. The illumination and the detection is performed along a scan path across a region, such that the first scattering data is spatially integrated over the region.

Another embodiment of the present invention provides an inspection apparatus comprising a radiation source, a detector, and a determining device. The radiation source is arranged to illuminate a region of a substrate with a radiation beam. The detector is arranged to detect scattered radiation to obtain first scattering data. The determining device is configured to compare the first scattering data with second scattering data, and based on the comparison, to determine the presence of a fault of the substrate at the region. The illumination and the detection is performed along a scan path across a region, such that the first scattering data is spatially integrated over the region.

A further embodiment of the present invention provides an article of manufacture including a computer readable medium having instructions stored thereon that, executed of which by a computing device, cause the computing device to perform operations comprising the following. Illuminating a region of a substrate with a radiation beam. Detecting scattered radiation to obtain first scattering data. Comparing the first scattering data with second scattering data. Determining, based on the comparison, the presence of a fault of the substrate at the region. The illumination and the detection is performed along a scan path across a region, such that the first scattering data is spatially integrated over the region.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
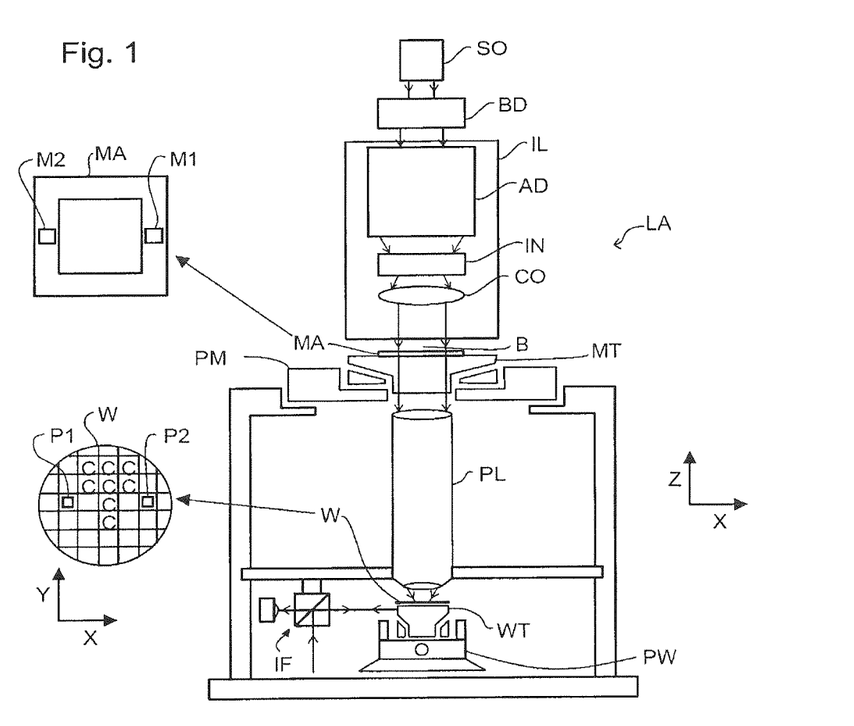
FIG. 1 depicts a lithographic apparatus.

FIG. 1 schematically depicts a lithographic apparatus. The apparatus comprises an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix. The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable beam directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
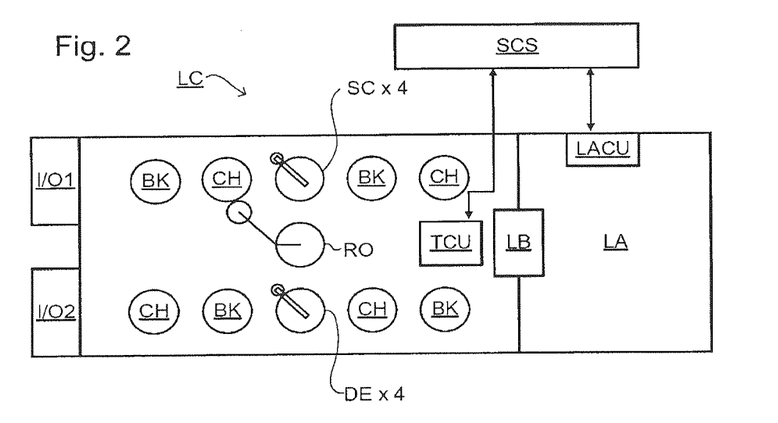
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
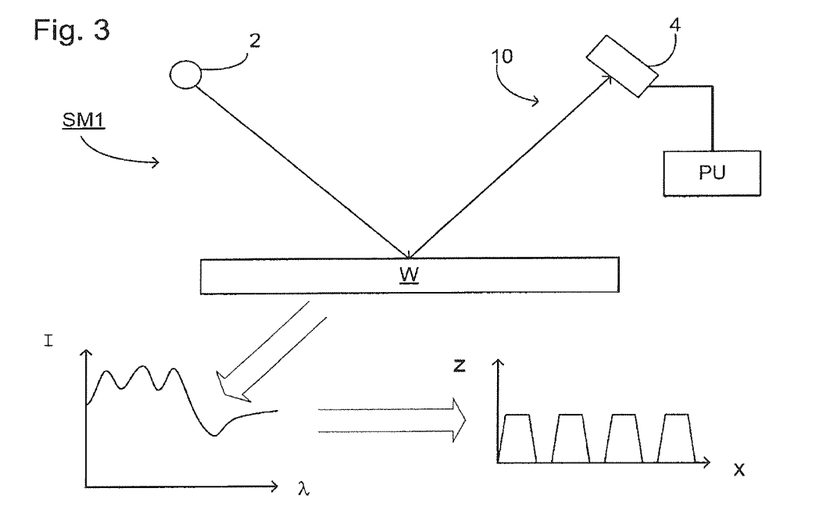
FIG. 3 depicts a first scatterometer.

FIG. 3 depicts a scatterometer which may be used in the present invention. It comprises a broadband (white light) radiation projector 2 which projects radiation onto a substrate W during a relative motion between the substrate W and the scatterometer 2, 4, the motion being controlled by the processing unit PU. The reflected radiation is passed to a spectrometer detector 4, which measures a spectrum 10 (intensity as a function of wavelength) of the specular reflected radiation. This measured data is spatially integrated along the path of motion during the measurement of the spectrum. From this data, the presence of faults in the structure or profile giving rise to the detected spectrum may be determined by comparison of the detected spectrum with a library of simulated spectra as shown at the bottom of FIG. 3. Such a scatterometer may be configured as a normal-incidence scatterometer or an oblique-incidence scatterometer.

Figure 4:
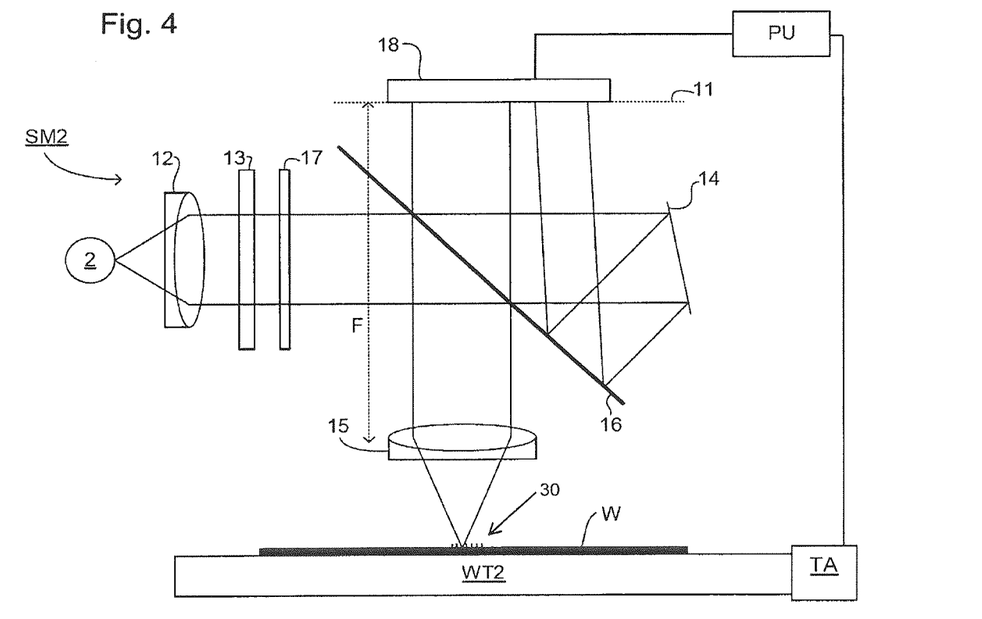
FIG. 4 depicts a second scatterometer.

Another scatterometer that may be used with the present invention is shown in FIG. 4. In this device SM2, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporate by reference herein in its entirety.

The processing unit PU controls a relative movement between the substrate W and the scatterometer SM2. The movement is controlled by the processing unit PU controlling motion of a wafer table or stage WT2 on which the substrate wafer W is located, using a wafer table actuator TA. The wafer table may be moved in X and Y directions independently.

The target pattern 30 on substrate W may be a strip of product pattern. The target pattern 30 may comprise a grating, which is printed such that after development, the bars are formed of solid resist lines. This pattern is sensitive to chromatic aberrations in the lithographic projection apparatus, particularly the projection system PL, and illumination symmetry and the presence of such aberrations will manifest themselves in a variation in the printed grating. The target pattern may alternatively be etched into the substrate, which is sensitive to process variations such as in the etching apparatus. The scatterometry data of the printed target pattern is used to detect faults in the pattern as described below.

Figure 5:
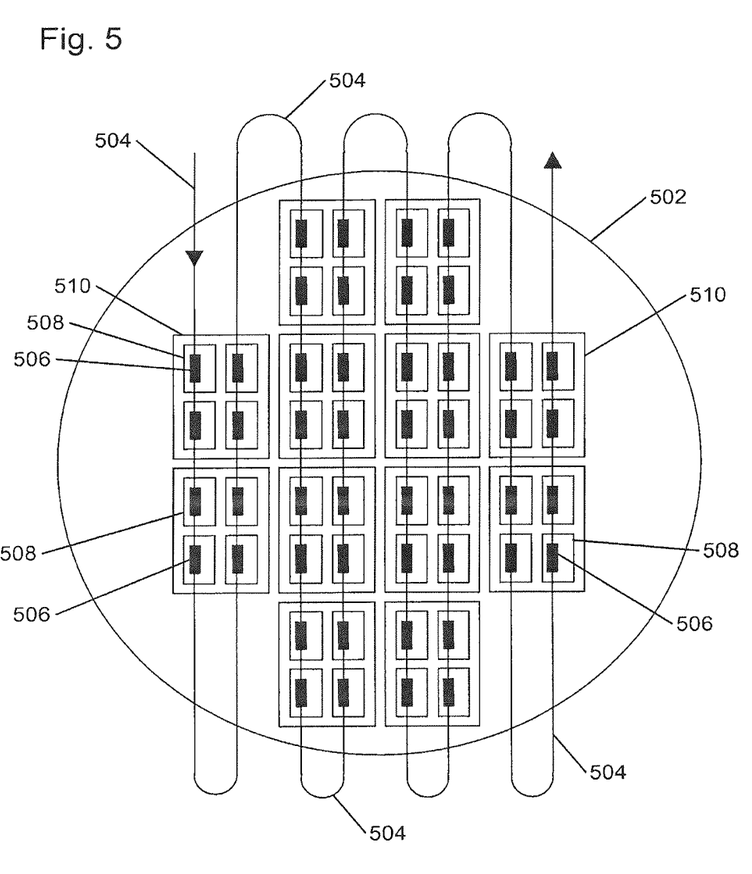
FIG. 5 illustrates a scan path trajectory over a wafer and strips where acquisition is performed on each die.

With reference to FIG. 5, in one embodiment of the present invention, the measurement spot of a radiation beam is scanned across the wafer substrate 502 in a scan path trajectory 504 comprising large (constant) velocity portions and the acquisition of an angle-resolved spectrum is taken at full scan speed. As a result, the measured spectrum is spatially integrated over the time-varying spectrum that occurs during the image acquisition. For example, if the scan speed is 1 m/s and the acquisition time is only 4 ms then the spot travels a distance of 4 mm. If the dies are 6 mm apart then the camera needs a frame rate of $1000 \text{ mm·s}^{-1}/6 \text{ mm} \approx 150$ fps which is challenging but feasible with current image sensor technology. In principle, the image acquisition can also be done in a step-and-scan fashion but this is probably not a preferred embodiment due to the risk of inducing vibrations. FIG. 5 shows, by way of example, the scan path trajectory 504 and the strips 506 where the image acquisition takes place (thick bars) The strips 506 are not to scale in FIG. 5. The width of a strip will be determined by the size of the part of the measurement spot over which spectrum data is gathered. This is typically 25 µm or less. The target pattern structures being inspected are a strip 506 in each die 508, with die arranged in a group 510 according to the reticle.

The structure to be inspected is typically periodic in the X and Y direction (like NAND flash). If a long acquisition is performed along a strip across the structure in the Y direction then Y position variation in the start and end positions of the strip have a relatively small effect on the acquired spatially integrated spectrum. Variation in the acquired spectrum resulting from spot position variation will primarily depend on the X position of the spot. Spot position variation will occur because no alignment of the spot to the wafer is performed along the high-speed scan path trajectory. X is horizontal and Y is vertical in the drawings.

Figure 6:
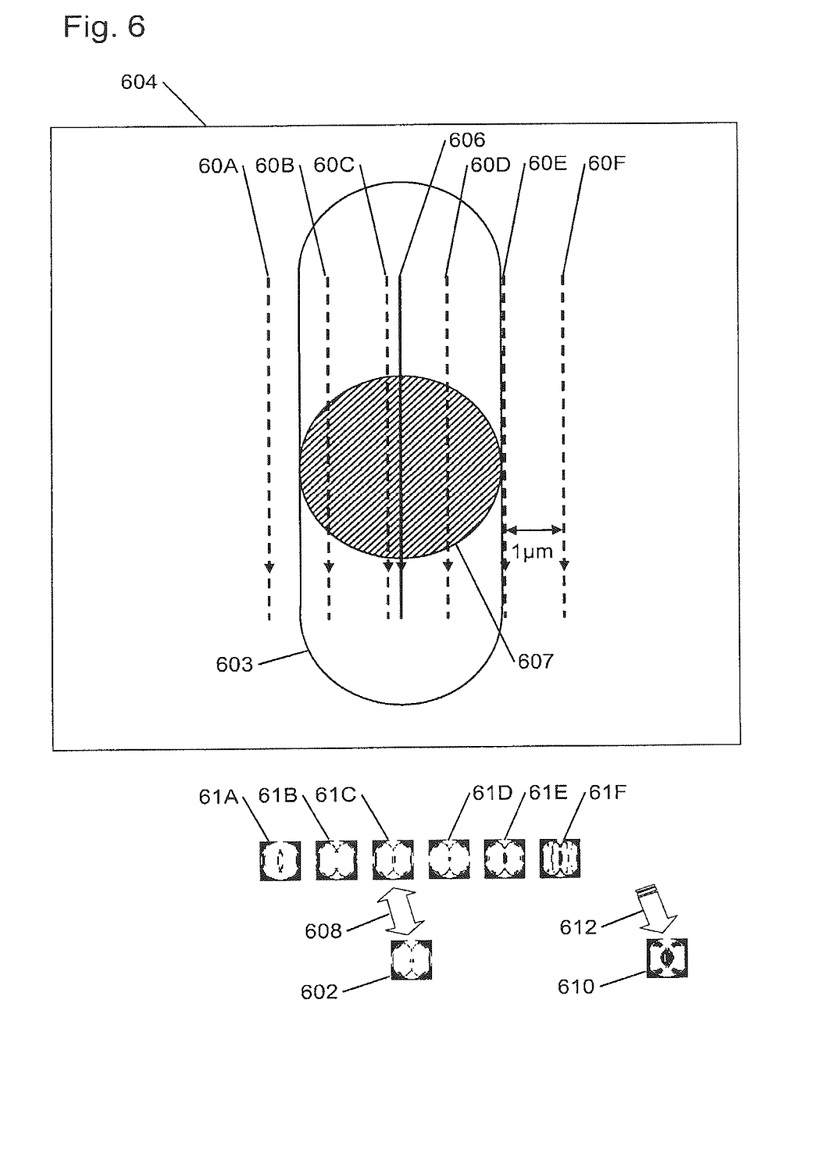
FIG. 6 illustrates a die with a measurement scan path and its measured spectrum being compared to a library of reference spectra with corresponding reference paths.

With reference to FIG. 6, a measured spectrum 602 of a strip 603 on a die 604 is acquired on a measurement scan path 606 of a moving measurement spot 607. The measured spectrum 602 is compared 608 with a set 61A to 61F of reference spectra that are stored in a library. These reference spectra 61A to 61F have been obtained for a range of scan paths 60A to 60F at respective X-positions on the die to allow for variation in the X position of the high-speed measurement spot. Although six reference scan paths are shown in FIG. 6, in practice a larger number may be used, such as 35, as discussed below. The reference spectra may be obtained either by computation from a model of the as-designed die or by measurement of one or more known good die on a reference wafer. Thus there is at least one reference spectrum per X position. The sampling distance along the X-direction is much smaller than the spot diameter and is approximately of the order of 1 µm. The X-range is at least the spot diameter plus the peak-to-peak wafer position uncertainty. The wafer position uncertainty is of the order of 10 µm and the spot diameter is of the order of 25 µm so in this example embodiment there is a library of only 35 entries (although only six are shown in FIG. 6) which is quite reasonable with respect to computation and storage requirements.

In order to cope with normal processing variations over the wafer this approach may be extended by making a separate library for multiple dies on the wafer. In its extreme form it is possible to make a library for every die on the wafer.

The comparison of the measured spectrum 602 with all the library entries 61A to 61F yields a good match 608 according to certain criteria like Goodness of Fit or mean-squared error, with library entry 61C. In the event of the die having a fault, resulting in another measured spectrum 610, then there is no spectrum in the library that meets the matching criteria and there is no match 612. In that case it is determined that that the die is suspect and that it may have experienced a processing error resulting in the fault.

Figure 7:
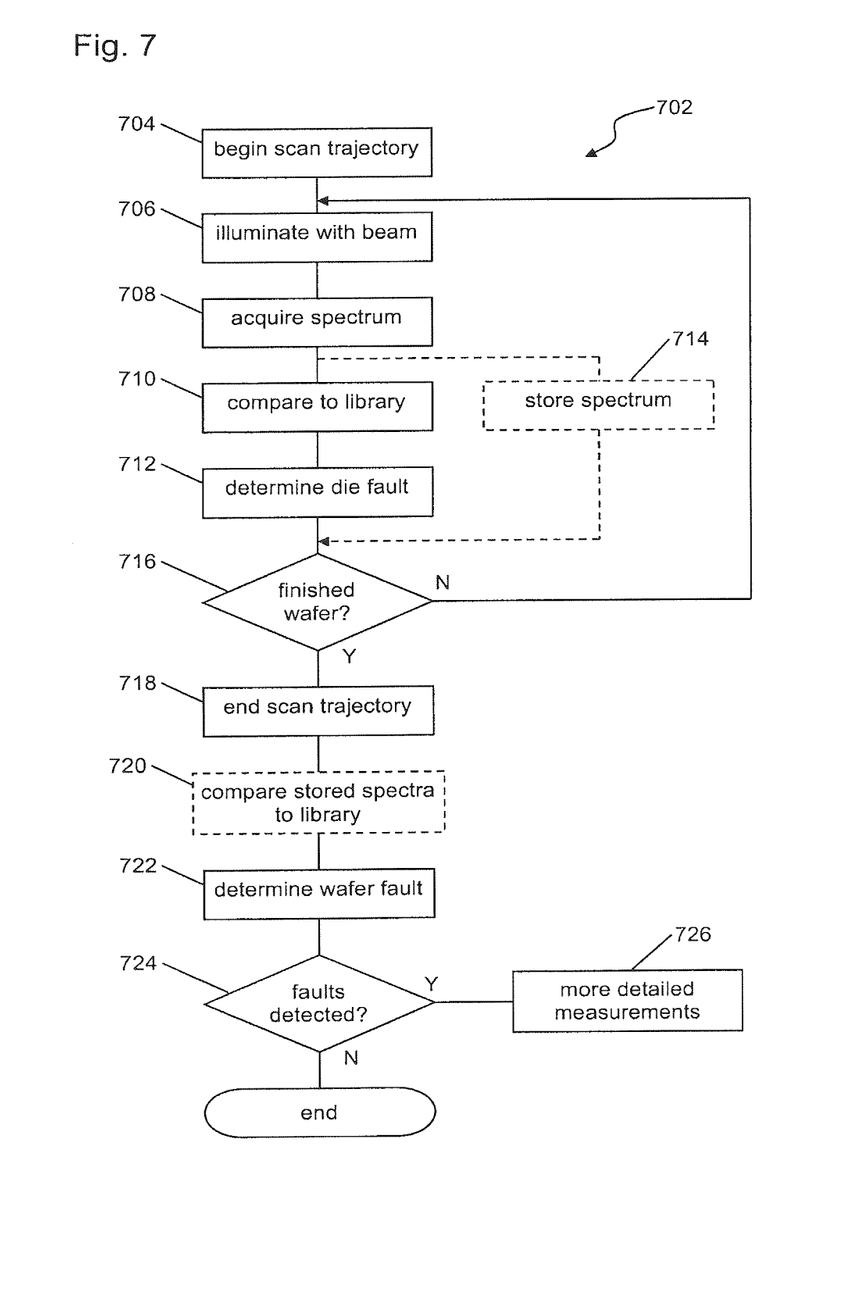
FIG. 7 is a flow chart of a method according to an embodiment of the present invention.

With reference to FIG. 7, a flowchart 702 is shown illustrating an embodiment of the present invention that is an inspection method for detecting a fault on a substrate. Under control of the processing unit PU (in FIGS. 3 and 4), the wafer stage (WT2 in FIG. 4) begins moving 704 according to the predetermined scan trajectory. The scan trajectory is set up to pass over at least part of one or more selected dies on the wafer. The light source 2 is switched on when passing over the predetermined strip of each die to illuminate 706 the strip on the surface of the substrate with the radiation beam. Thus the illumination 706 and detection 708 is performed along a scan path crossing the strip region. By detecting scattered radiation along the strip scattering/diffraction data is obtained or acquired 708 at each selected die, in the form of a spatially integrated or averaged angle resolved spectrum. The scan path is preferably linear along the strip, although non-linear paths or strips may also be used. The strip is typically in line with the edge a die, to match the orientation of the pattern on the die, however, other orientations may be used in order to match the layout of the product pattern on the die. The location of the strips are predetermined and selected to measure suitable structures on the die. Such structures may have periodic or grating-like features with a periodicity perpendicular to the scan path. On a die there may be more than one strip along the scan path trajectory corresponding to the location of such suitable structures. This may be achieved by breaking up the strip by switching the beam and/or detector on and off repeatedly.

Each acquired spectrum is compared 710 with one or more measured or calculated reference spectrum for that die. This may be done for a library of reference spectra corresponding to a range of positions, perpendicular to the relative motion's direction, spanning a distance calculated as the position's uncertainty plus the size of the radiation beam. Based on the comparison 710 the presence of a fault of the wafer at the strip is determined 712 and the result stored. This determination 712 may overlap in time with some or all of the movement to the next die. Furthermore, the determination 712 may overlap in time with some or all of the illumination 706 and acquisition 708 of the next die.

Alternatively (as shown by the dotted lines), the acquired spectrum is stored 714 for later analysis, or the analysis is done in parallel with the acquisition and movement, for example by a different processor.

If the wafer is not finished 716, then the scanning trajectory continues to another acquisition site, otherwise the scan trajectory ends 718. If the comparison and determining steps 710 and 712 have not been done, then the comparison of each acquired spectrum, stored in step 714, may be performed in a batch 720 against the library. If the wafer is determined 724 to be suspect because of a poor match then a more detailed measurement can be done 726 on one or more of the metrology targets in the neighborhood of a suspect die, for example in the adjacent scribe lane.

The handling of the measured spectra including logging, charting, alerting and decision making about further measurements may be performed using methods known to one skilled in the art for handling other metrology data, such as critical dimensions (CDs).

However, unlike conventional sampled CD measurements, the present invention offers large wafer coverage for all wafers in a lot and this maximizes the chance to detect localized wafer excursions. This results in a more robust early fault detection. The present invention is suited for use in scatterometry inspection apparatus that uses fast balance-mass stages that can move the wafer at high speed with respect to the radiation beam.

Figure 8:
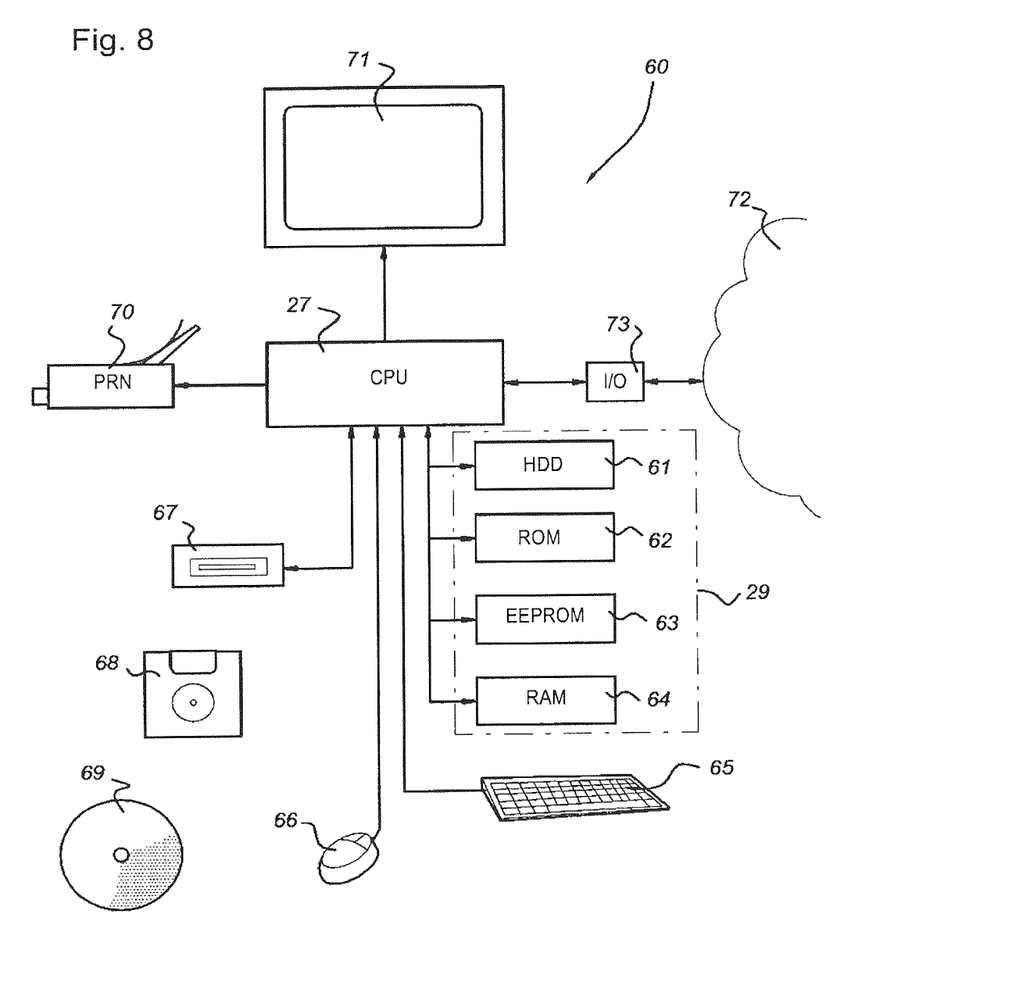
FIG. 8 depicts a computer assembly that may be used in apparatus according to an embodiment of the present invention.

The method according to the present invention may be implemented under the control of a computer program, running on a processor. It should be understood that the processor running the computer program to implement the methods in the previous embodiments may be a computer assembly 60 as shown in FIG. 8. The computer assembly 60 may be a dedicated computer in the form of a processing unit PU in embodiments of the assembly according to the invention or, alternatively, for example, be a central computer controlling the lithographic projection apparatus. The computer assembly 60 may be arranged for loading a computer program product comprising computer executable code. This may enable the computer assembly 60, when the computer program product is downloaded, to control aforementioned uses of a lithographic apparatus with embodiments of the image sensor.

The memory 29 connected to processor 27 may comprise a number of memory components like a hard disk 61, Read Only Memory (ROM) 62, Electrically Erasable Programmable Read Only Memory (EEPROM) 63 en Random Access Memory (RAM) 64. Not all aforementioned memory components need to be present. Furthermore, it is not essential that aforementioned memory components are physically in close proximity to the processor 27 or to each other. They may be located at a distance away.

The processor 27 may also be connected to some kind of user interface, for instance a keyboard 65 or a mouse 66. A touch screen, track ball, speech converter or other interfaces that are known to persons skilled in the art may also be used.

The processor 27 may be connected to a reading unit 67, which is arranged to read data, e.g., in the form of computer executable code, from and under some circumstances store data on a data carrier, like a floppy disc 68 or a CDROM 69. Also DVD's or other data carriers known to persons skilled in the art may be used.

The processor 27 may also be connected to a printer 70 to print out output data on paper as well as to a display 71, for instance a monitor or LCD (Liquid Crystal Display), of any other type of display known to a person skilled in the art.

The processor 27 may be connected to a communications network 72, for instance a public switched telephone network (PSTN), a local area network (LAN), a wide area network (WAN) etc. by means of transmitters/receivers 73 responsible for input/output (I/O). The processor 27 may be arranged to communicate with other communication systems via the communications network 72. In an embodiment of the invention external computers (not shown), for instance personal computers of operators, can log into the processor 27 via the communications network 72.

The processor 27 may be implemented as an independent system or as a number of processing units that operate in parallel, wherein each processing unit is arranged to execute sub-tasks of a larger program. The processing units may also be divided in one or more main processing units with several subprocessing units. Some processing units of the processor 27 may even be located a distance away of the other processing units and communicate via communications network 72.

Although specific reference may be made in this text to the use of inspection methods and apparatus in the manufacture of ICs, it should be understood that the inspection methods and apparatus described herein may have other applications, such as determining faults in the manufacture of integrated optical systems, guidance and detection patterns for magnetic domain memories, flat-panel displays, liquid-crystal displays (LCDs), reticles, thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the teem substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method comprising:
illuminating a region of a substrate with a radiation beam;
detecting scattered radiation to obtain first scattering data;
comparing the first scattering data with second scattering data from a library, wherein the library comprises scattering data for a range of positions perpendicular to a direction of a scan path; and
determining, based on the comparison, the presence of a fault of the substrate at the region,
wherein the illumination and the detection is performed along the scan path across the region, such that the first scattering data is spatially integrated over the region.

2. The method of inspection according to claim 1, wherein the region comprises a strip.

3. The method of inspection according to claim 1, wherein the first and second scattering data comprise diffraction spectra.

4. The method of inspection according to claim 3, wherein the diffraction spectra are angle resolved.

5. The method of inspection according to claim 1, wherein the second scattering data is obtained by measurement of a reference region of a substrate.

6. The method of inspection according to claim 5, wherein the reference region is a strip.

7. The method of inspection according to claim 1, wherein the second scattering data is obtained by calculation from a model of a reference region.

8. The method of inspection according to claim 7, wherein the reference region is a strip.

9. The method of inspection according to claim 1, wherein the range of positions perpendicular to the direction of the scan path spans a distance calculated using a position uncertainty of the radiation beam and a size of the radiation beam.

10. An inspection apparatus comprising:
a radiation source configured to illuminate a region of a substrate with a radiation beam;
a detector configured to detect scattered radiation to obtain first scattering data; and
a determining device configured to:
compare the first scattering data with second scattering data from a library wherein the library comprises scattering data for a range of positions perpendicular to a direction of a scan path, and
determine the presence of a fault of the substrate at the region based on the comparison,
wherein the illumination and the detection are performed along the scan path across the region, such that the first scattering data is spatially integrated over the region.

11. The inspection apparatus according to claim 10, wherein the region comprises a strip.

12. The inspection apparatus according to claim 10, wherein the first and second scattering data comprise diffraction spectra.

13. The inspection apparatus according to claim 12, wherein the diffraction spectra are angle resolved.

14. The inspection apparatus according to claim 10, wherein the second scattering data is obtained by measurement of a reference region of a substrate.

15. The inspection apparatus according claim 14, wherein the reference region is a strip.

16. The inspection apparatus according to claim 10, wherein the second scattering data is obtained by calculation from a model of a reference region.

17. The inspection apparatus according to claim 16, wherein the reference region is a strip.

18. The inspection apparatus according to claim 10, wherein the range of positions perpendicular to the direction of the scan path spans a distance calculated using a position uncertainty of the radiation beam and a size of the radiation beam.

19. An article of manufacture including a computer readable medium having instructions stored thereon that, executed of which by a computing device, cause the computing device to perform operations comprising:
illuminating a region of a substrate with a radiation beam;
detecting scattered radiation to obtain first scattering data;
comparing the first scattering data with second scattering data from a library, wherein the library comprises scattering data for a range of positions perpendicular to a direction of a scan path; and
determining, based on the comparison, the presence of a fault of the substrate at the region,
wherein the illumination and the detection is performed along the scan path across the region, such that the first scattering data is spatially integrated over the region.

* * * * *